United States Patent [19]

Ohyama et al.

[11] Patent Number: 5,041,224

[45] Date of Patent: Aug. 20, 1991

[54] ION PERMEABLE MEMBRANE AND ION TRANSPORT METHOD BY UTILIZING SAID MEMBRANE

[75] Inventors: Junji Ohyama, Yamato; Harumi Iwashita, Atsugi; Kinya Kato, Yokohama; Nobuko Yamamoto, Isehara; Masanori Sakuranaga, Atsugi; Tsunehiro Kanno, Isehara; Yasuko Tomida, Ebina, all of Japan

[73] Assignee: Canon Kabushiki Kaisha, Tokyo, Japan

[21] Appl. No.: 329,811

[22] Filed: Mar. 28, 1989

[30] Foreign Application Priority Data

Mar. 28, 1988 [JP] Japan .................. 63-071884

[51] Int. Cl.5 ............................ B01D 69/00
[52] U.S. Cl. ................. 210/500.27; 430/332
[58] Field of Search .......... 210/638, 500.27; 422/68, 98; 430/338, 332; 204/153.1

[56] References Cited

U.S. PATENT DOCUMENTS 3,966,580 6/1976 Janata et al. .................. 204/195 B
4,215,182 7/1980 Ang et al. ........................ 429/15
4,356,256 10/1982 O'Brien et al. ............... 430/338 X

FOREIGN PATENT DOCUMENTS 2284632 9/1976 France .

OTHER PUBLICATIONS

Yager, U.S. Statutory Invention Registration No. H201, 1–1987.
K. Suzuki, et al., "Ion–Selective Electrodes Based on Natural Carboxylic Polyether Antibiotics", Analytical Chemistry, vol. 60, No. 17, (pp. 1714–1720) 1988.
Patent Abstracts, Japan, vol. 13, No. 306 (p. 897) (3654) Jul. 13, 1989, for Appln. No. 1-180854, published Sep. 24, 1987.

*Primary Examiner*—Frank Spear
*Attorney, Agent, or Firm*—Fitzpatrick, Cella Harper & Scinto

[57] ABSTRACT

An ion permeable membrane, comprising two or more groups of substances having different sensitive wavelength regions in a lipid membrane, is provided.

27 Claims, 5 Drawing Sheets

ION PERMEABLE MEMBRANE AND ION TRANSPORT METHOD BY UTILIZING SAID MEMBRANE

BACKGROUND OF THE INVENTION

1. Field of the Invention

This invention relates to a selective ion permeable membrane by photoirradiation utilizing substances which transport ions by absorption of light and an ion transporting method by utilizing the membrane.

2. Related Background Art

Presently, selective permeation of ion has been known as one function of biological membrane, and researches are under progress for obtaining dialysis membranes or various sensors by imparting the function analogous to a biological membrane by such method that a substance having active transportability of an ion is held within a thin film by utilizing such selective permeation. Also, since the membrane utilizing the above principle can be utilized for a device having the function of converting easily the ion concentration difference across the membrane, the so called membrane potential into electrical signals by combination with ion sensitive electrodes, etc., a device by use of said membrane has been proposed to be applied as the chemical device which converts chemical signals to electrical signals. As the device which uses a protein as the ion active transportable substance, for example, a constitution of biochemical device such as sensor for embedding in biological membrane is disclosed in Japanese Patent Laid-open No. 62-11158.

Whereas, if a photoirradiation is used for effecting an ion permeability control, not only the external control method can become easy, but also, for example, a chemical device which can effect photoelectric conversion with small exothermic quantity can be realized. A ion permeable membrane having an excellent volume efficiency and an energy efficiency, maintaining and good controllability is promising in the future as well as the converting device in the field of optical communication.

Also, in controlling a membrane ion permeability by photoirradiation, it is desirable to set the wavelength of the incident light as desired. Further, it is desirable as a matter of course that the membrane ion permeability should not limited to only one direction, but can select the direction of permeation and yet can select it depending on the wavelength of the incident light.

However, at present, no device sufficiently controlled in an ion permeability by photoirradiation has been obtained.

SUMMARY OF THE INVENTION

Accordingly, an object of the present invention is to provide an ion permeable membrane of which control of ion permeability can be set as desired by photoirradiation.

More specifically, the present invention provides an ion permeable membrane, comprising two or more groups of substances having different sensitive wavelength regions in a lipid membrane.

Also, the present invention provides an ion permeable membrane, comprising further an ionophore and two or more groups of substances having different sensitive wave length regions in a lipid membrane.

Further, the present invention provides an ion transport method utilizing an ion permeable membrane, which comprises varying the ion permeability of said ion permeable membrane by irradiating a light on the above ion permeable membrane by selecting the wavelength of said light.

Also further, the present invention provides an ion transport method utilizing an ion permeable membrane containing further an ionophore, which comprises varying the ion permeability of said ion permeable membrane by irradiating a light on the above ion permeable membrane by selecting the wavelength of said light.

DETAILED DESCRIPTION OF THE PREFERRED EMBODIMENTS

The present inventors are interested in the fact that selectivity (specificity) and reaction efficiency in biochemical reactions as can be seen in biological materials are extremely high as compared with physical or chemical reactions. They have investigated an ion permeable membrane, for which the wavelength region to be irradiated can be freely selected, and also which can be controlled in ion permeability to a specific ion with the photoirradiation energy at high sensitivity, and yet can select the directionality of an ion permeation corresponding to the incident light, and also a control method thereof.

In the course of such investigation, the present inventors were interested in photoreceptive protein which exist in retina of animals, etc. and are a substance capable of effecting photodetection by performing a substance transport in a living cell with a very high sensitivity and a high resolution to a visible light, and have used a photoreceptive protein having the function and the structure similar thereto, yet capable of existing relatively stable at normal temperature, being held within a lipid membrane. They have realized the above function by that an ion transport substance (ionophore), which has a structure and a function of an antibiotic, produced by a microorganism, having an ion transport ability, or of a similar substance to an antibiotic, and which is occurring naturally or obtained by synthesis, and is held within a lipid membrane in which the above photoreceptive proteins are also incorporated.

As the substance having the function transporting various ions by absorption of light as herein mentioned, photoreceptive proteins can be included, but any of various photoreceptive proteins or analogues thereof having such function can be utilized without limitation as to its kind.

Typical examples of photoreceptive proteins may include so called visual substances, namely pigment proteins existing in animal retina, and these comprise a chromophore portion (e.g. retinal) and a protein (e.g. opsin), having the function of receiving light in retinal neuroepithelial layer of animal and replacing it with a certain membrane ion permeable change. As such proteins, for example, rhodopsin, porphyropsin, iodopsin, etc. have been extracted and purified. Also, as substances having similar functions to visual substances, there are bacteriorhodopsin and halorhodopsin existing in cell membranes of halophile, and these are preferably relatively simpler to handle.

Bacteriorhodopsin is the main component of the proteins of cell membrane (purple membrane) of a highly halophilic bacterium *Halobacterium halobium* belonging to the genus Halobacterium, which contains retinal as the chromophore group and has the function transporting protons by absorption of a visible light (proton pump ability) [A. Danon, W. Stoeckenius: Proc. Natl. Acad. Sci., USA, 71, 1234 (1974)].

Bacteriorhodopsin can be extracted, for example, as purple membrane from highly halophilic bacterium by use of the method of Oesterhelt and W. Stoeckenius (Method in Enzymology, 31, 667 (1974)), and further removing lipids from the purple membrane according to the method as described in K. S. Huang, H. Bayley and H. G. Khorana (Proc. Natl. Acad. Sci., USA 77, 323 (1980), resulting in purified bacteriorhodopsin.).

On the other hand, halorhodopsin is a protein found from a mutant of highly halophilic bacterium such as $R_{1m}$, $L_{33}$, etc. and has the property of transporting chloride ions by receiving a visible light [A. Y. Matsuno and Y. Mukohata: Biochem. Biophys. Res. Commun., 78, 237 (1977); R. E. MacDonald, R. U. Greene, R. D. Clark, E. V. Lindley: J. Biol. Chem., 254, 11831 (1979)].

This halorhodopsin can be obtained from highly halophilic bacterium by use of the method as described in, for example, Y. Mukohata, Y. Sugiyama and Y. Kaji, J. Usukura and E. Yamada (Photochem. Photobiol., 33, 539 (1981)).

Also, a naturally occurring photoreceptive protein separate from cells can be varied in the structure without damaging its function to form a derivative changed in the sensitive wavelength, and can be used in the present invention.

Typically, the retinal portion can be replaced to change the light absorption wavelength. Specific examples forming such derivatives in rhodopsin may include, for example, the cases in which the retinal portion is changed to:

a) all-trans-retinal, thereby forming bacteriorhodopsin with the absorption maximum wavelength of 570 nm [P. Townor, W. Gaerther, et al, Eur. J. Biochem., 117, 353 (1981)];

b) 13-cis-retinal, thereby forming bacteriorhodopsin with the absorption maximum wavelength of 550 nm [ibid.];

c) 5,6-dihydroretinal, thereby forming bacteriorhodopsin with the absorption maximum wavelength of 475 nm [R. Mao, R. Govindjee, et al, Biochemistry, 20, 428 (1981)];

d) retro-γ-retinal, thereby forming bacteriorhodopsin with the absorption maximum wavelength of 430 nm [K. S. Huang, H. Baylay, et al, Fed. Proc., 40, 1659 (1981)];

e) 3,4-dihydroretinal, thereby forming bacteriorhodopsin with the absorption maximum wavelength of 593 nm [F. Tokunaga, T. Ebrey, Biochemistry, 17 (1978)]; etc.

Further, the amino acid sequence of bacteriorhodopsin has been already clarified [Yu. A. Ovchinnikov, N. G. Abdulaev, et al, Bioorg. Khim., 4, 1573 (1978)] and also the sequence of the bacteriorhodopsin gene of halobacterium [R. J. Dunn, J. M. McCoy et al, Proc. Natl. Acad. Sc., 78, 6744 (1981)]. From these knowledges, a recombinant DNA can be constructed and a protein analogue with substituted amino acid sequence of bacteriorhodopsin can be synthesized [N. R. Hackett, L. J. Stern, et al., J. Biol, Chem., 262, 9277 (1987)], and such analogous photoreceptive proteins substance can be also used in the present invention. Depending on the constitution of the ion permeable membrane requiring two or more different light absorption wavelength regions, substances may be selected and used from among the analogous photorecptive proteins as described above.

In the present invention, the lipid membrane holding the photoreceptive substances exhibits ion impermeability, with the inner portion of the membrane exhibiting hydrophobic property and the outer surface hydrophilic property.

As the material for the lipid membrane, known amphophilic compounds capable of constituting monomolecular film or polymolecular film can be utilized. These lipid molecules having film forming ability can be constituted by a long chain alkyl group with 8 or more carbon atoms and a hydrophilic group, the hydrophilic group being either one of a cation such as:

an anion such as:

a nonion such as:

an ampholytic ion such as:

Among these, glycerophospholipids such as phosphatidylcholine (lecithin), phosphatidylethanolamine, disphophatidylglycerol, etc.; sphingophospholipids such as sphingomyelin, ceramidesiliatin, etc.; sphingoglycolipids such as cerebroside, sulfatide, ceramideoligohexoside, etc.; and glyceroglycolipids such as glycosyldiacyl glycerol, etc. which contains carbohydrate as the hydrophilic group are lipids constituting cell membranes, and therefore they can be particularly suitable for forming artificial lipid membranes holding the photoreceptive substance by incorporating the photoreceptive substance as described above and exhibiting the function of said protein with a good efficiency.

As a typical example, there is soybean lecithin. This can be produced according to the method of [Y. Kagawa and E. Racker, J. Biol. Chem 246, 5477 (1971)]. Various lipids having the function as the lipid as described above can be utilized, and their kinds are not limited.

The lipid membrane as herein mentioned is formed from the lipid material as described above, and that comprising monomolecular layer of lipid, or constituted of two layers laminated of monomolecular films of lipid (lipid double layers film) or 3 or more layers laminated of monomolecular films of lipid (lipid bilayer) can be utilized. However, each monomolecular layer may be polymerized by light-irradiation, for example, UV-irradiation, etc.

Among them, when a photoreceptive protein is held within a lipid bilayer film, a photosensitive dye protein can be reconstituted in the form similar to the structure in natural cells, and its function can be conveniently utilized effectively. Also, bacteriorhodopsin exists in a lipid layer called purple membrane of halobacterium, and the fragment of the lipid-protein composite can be conveniently extracted.

For forming a composite of a photoreceptive substance such as bacteriorhodopsin with a lipid, it can be obtained by use of, for example, the method as described in [E. Racker and W. Stoeckenius, J. Biol. Chem., 249, 662 (1974)] or [K. S. Huang, H. Bayley and H. G. Khorana, Proc. Natl. Acad. Sci., USA, 77, 323 (1980)], by suspending the lipid as described above in a solution with an appropriate salt concentration, adding a desired photosensitive dye protein into the solution and permitting it to be incorporated into the lipid film formed during formation of liposome, while under sonication treatment if desired.

From the product thus obtained, the proteoliposome having the photosensitive dye protein incorporated therein can be separated and purified by means of the column chromatography method, the ultracentrifugation method according to the sucrose density gradient method as described in [C. Lind., Bo. Hojeberg and H. G. Khorana, J. Biol. Chem., 256, 8298 (1981)].

The proteoliposome thus purified is adsorbed and fused into a lipid-bilayer, which is previously prepared by dipping lipid molecules in an appropriate solvent, to form a light-responsive ion permeable membrane.

Alternatively, as known in purple membrane, proteoliposome is spread in a water Langmuir trough to be attached onto the lipid-bilayer, by which a protein lipid bimolecular composite film can be formed. In this case, a plane film can be obtained, which forms a hydrophilic surface on the substrate side by attaching it on the substrate according to horizontal attachment, or a hydrophobic surface on the substrate side by attachment according to the vertical dipping method. A proteoliposome holding a protein different from the protein within the membrane can be adsorbed and fused to the membrane. According to this method, a composite film incorporating a photoreceptive protein (light-responsive ion permeable membrane), in which ion permeation directions are reversed within one layer can be formed. Then, said composite membrane can sustain different kinds of photoreceptive proteins keeping an orientation the same as the respective kind within the lipid membrane.

Figure 3:
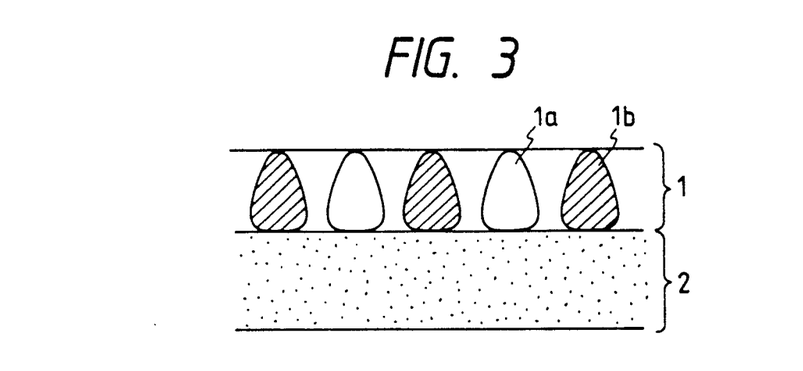
FIG. 3 and FIG. 4 are schematic sectional views showing the constitution of the ion permeable membrane of the present invention.
Figure 4:
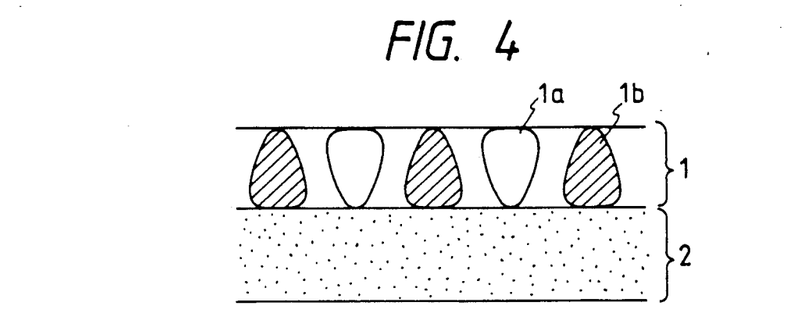

FIG. 3 and FIG. 4 illustrate schematically the constitution of the ion permeable membrane of the present invention.

In the Figures, the symbol 1 shows an ion permeable membrane, 1a and 1b two different photoreceptive proteins, and 2 a porous supporting substrate. As the substrate, collagen, cellulose, porous glass, etc. can be utilized.

Next, the method of controlling the light-responsive ion permeable membrane thus constituted is to be described by referring to the drawings.

Figure 1:
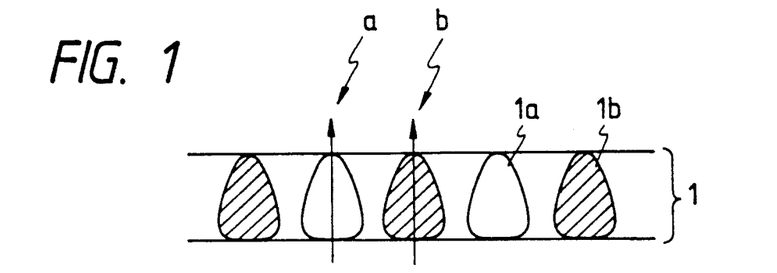
FIG. 1 and FIGS. 2A and 2B are schematic partial sectional views of the ion permeable membrane for illustration of the principle of the ion permeable membrane of the present invention.

FIG. 1 is a schematic sectional view of a constitutional example of the ion permeable membrane of the present invention.

According to the method as shown above, a light-sensitive permeable membrane having the two kinds of photoreceptive proteins 1a and 1b which react to the different wavelength regions respectively oriented in the same direction within 2 molecules of lipid is formed. The two different photoreceptive proteins 1a and 1b are selected so that their absorption maximum wavelengths may be positioned at, for example, shorter wavelength region $\lambda_1$ for 1a, and longer wavelength region $\lambda_2$ for 1b. In the Figure, a and b show respectively the shorter wavelength of side incident light and the longer wavelength side incident light. The ion permeability of this membrane can be realized in broader wavelength region expanded as compared with the case where 1a or 1b exists alone. Also, according to this constitution, the ion quantity permeating corresponding to each wavelength can be controlled.

Figure 2A:
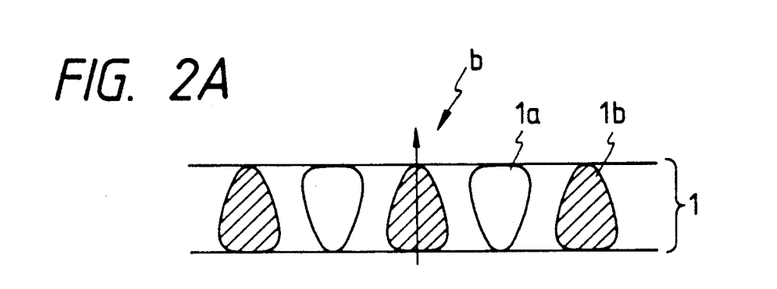
Figure 2B:
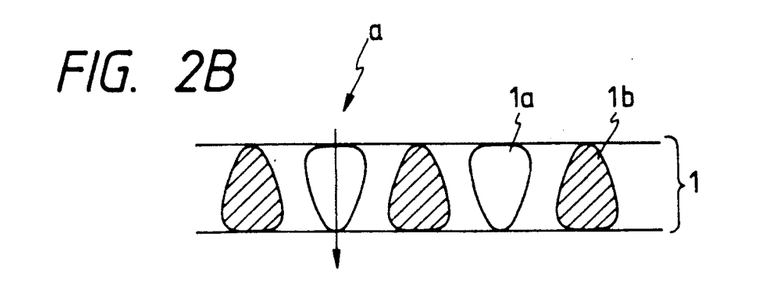

FIGS. 2A and 2B are schematic sectional views showing another constitutional example of the present invention.

The permeable membrane 1 in this example has two photoreceptive proteins 1a and 1b which react to different wavelength regions and orient the ions to be transported in opposite directions to each other. In this membrane, the directionality of ion transport can be freely selected by, for example, switching the exposing light wavelength from $\lambda_1$ to $\lambda_2$. Also, upon utilizing the difference of this directionality by selecting the photoreceptive proteins 1a and 1b so that the light absorption bands of 1a and 1b may adequately overlap each other, wavelength selectivity to the light with wavelengths near $\lambda_1$ or $\lambda_2$ can be improved to great extent.

Further, when an ionophore is incorporated in the ion permeable membrane as described above (ion permeable membrane having two or more kinds of photoreceptive proteins sensitive respectively to different wavelength regions held within lipid membrane), an ion permeable membrane capable of migrating different kinds of ions can be formed. The ionophore as herein mentioned refers to a substance which, when the above photoreceptive protein transports an ion by photoirradiation, and generates gradient across the membrane, transports another kind of ion at the same time using the concentration gradient generated thereby as the driving force (ion passive transport type).

Specifically, examples of the ionophore having ion transportability may include naturally occurring oligopeptides originated from microorganism such as gramicidins, valinomycin, nonactin, monactin, nijericin, aramethicin, monendin, A23187, X-537A, etc., or otherwise cyclic oligopeptides artificially synthesized, etc.

Also, there may be included organic compounds such as cyclic polyethers (crown ethers), polyetherpolyamines (cryptands), cyclams, etc. Various ionophores can be utilized without limitation as ionophore, provided that they have the function as described above.

Figure 5:
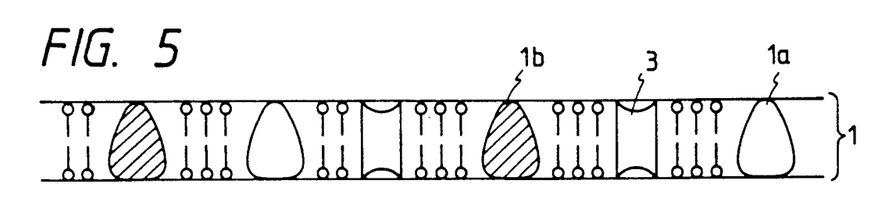
FIG. 5 and FIG. 6 are sectional views showing the constitution of the ion permeable membrane of the present invention.
Figure 6:
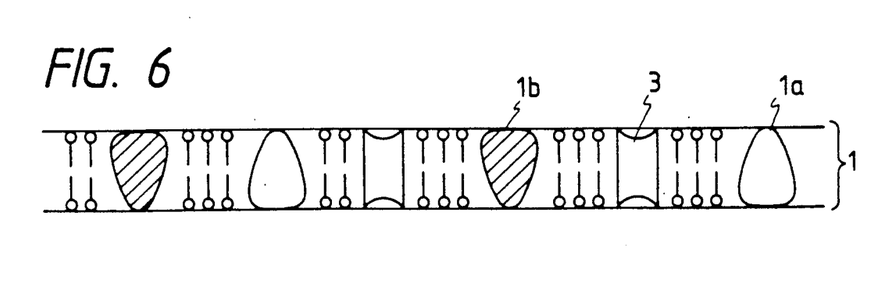

FIG. 5 and FIG. 6 show schematic sectional views of the constitution of the ion permeable membrane of the present invention.

In the Figures, the symbol 1 shows an ion permeable membrane, 1a and 1b two different photoreceptive proteins and 3 an ionophore.

Next, the method of controlling the photoreceptive ion permeable membrane thus constituted is to be described.

Figure 7:
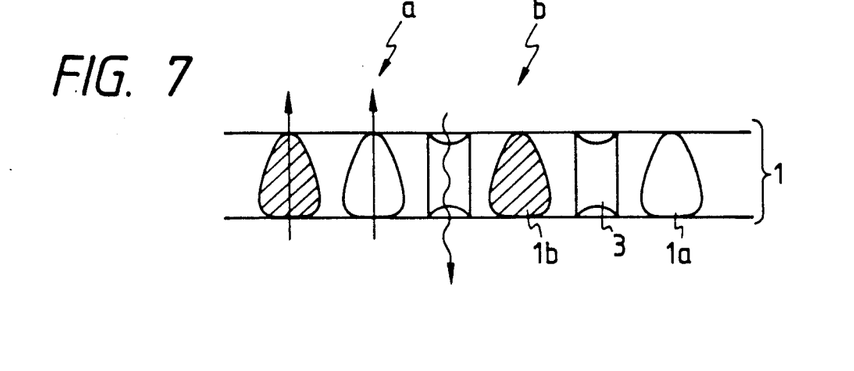
FIG. 7 and FIGS. 8A and 8B are schematic sectional views for illustration of the principle of the ion permeable membrane of the present invention.

As shown in FIG. 7, the two different photoreceptive proteins 1a and 1b and the ionophore 3 form the ion permeable 1 oriented within the lipid bilayer.

The two different photoreceptive 1a and 1b are oriented in the same ion permeation direction. The two different photoreceptive proteins 1a and 1b are selected so that their absorption maximum wavelengths may be positioned, for example, at the shorter wavelength side $\lambda_1$ for 1a and at the longer wavelength side $\lambda_2$ for 1b. In the Figure, a and b show respectively the shorter wavelength side light and the longer wavelength side light, respectively. The ion permeability of this membrane is realized in broader wavelength region expanded as compared with the case when 1a or 1b exists alone.

Further, by introduction of the ionophore, it is possible to change permeability of the second ion different from that of the first ion by use of the concentration gradient generated by the active transport of the first ion performed by 1a or 1b by photoirradiation as the driving force.

Figure 8A:
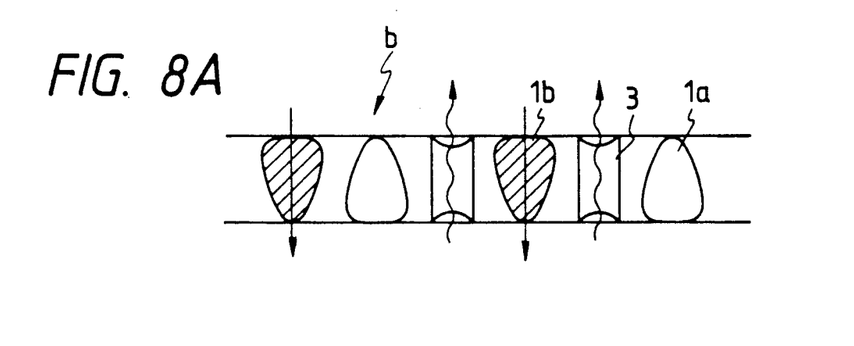
Figure 8B:
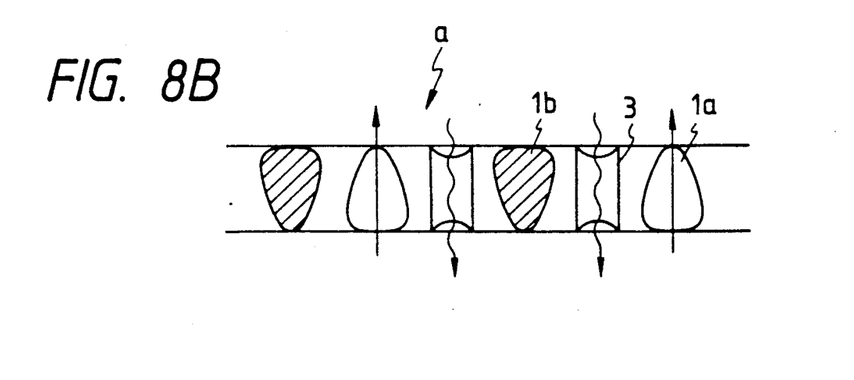

FIGS. 8A and 8B are schematic sectional views showing another constitutional example of the present invention.

In said Figures, two different photoreceptive proteins 1a and 1b are oriented in ion permeation directions opposite to each other.

In this membrane, the directionality of ion transport can be selected freely by, for example, switching the exposing light wavelength from $\lambda_1$ to $\lambda_2$. Also, utilizing the difference in directionality, by selecting the photoreceptive proteins 1a and 1b so that the light absorption bands of 1a and 1b may overlap adequately each other, a wavelength selectivity to the light with wavelengths near $\lambda_1$ or $\lambda_2$ can be improved to great extent.

Further, by introduction of ionophore, the directionality of ion transport of the second ion different from that of the first ion can be selected with the concentration gradient generated by active transport of the first ion performed by 1a or 1b as driving force.

The present invention is described in detail below by referring to Examples, but these are not limitative of the scope of the present invention at all.

EXAMPLE 1

The purple membrane extracted from *Halobacterium halobium* R1 strain by the method of Oesterhelt et al as described above was treated with a surfactant Triton X-100 (manufactured by Wako Junyaku Kogyo Co.) according to the method of Huang et al to remove lipids from the extracted purple membrane and obtain bacteriorhodopsin which was the protein component, of purple membrane. Chromophore group of the bacteriorhodopsin thus purified was substituted with naphthylretinal which was a kind of retinal analogues according to the method of Tokunaga et al [F. Tokunaga and T. Iwasa, Membrane, 9, 73 (1984)]. While the maximum absorption wavelength of bacteriorhodopsin was around 560 nm, the maximum absorption wavelength of the bacteriorhodopsin analogue having naphthylretinal as the chromophore group was made to be distributed from 442 nm to 503 nm depending on the mixing ratio. The bacteriorhodopsin analogue exhibited a proton active transport activity by photoirradiation similarly as bacteriorhodopsin. By mixing bacteriorhodopsin and its analogue in equal amounts, and by use of the soybean phospholipid asolectin purified by the method of Kagawa et al [Y. Kagawa and E. Racker, J. Biol. Chem., 246, 5477 (1971)], mixed proteoliposomes were constituted based on the method of Huang et al as described above. The proteoliposomes were irradiated with a monochromatic visible light obtained from a mercury lamp light passing through a monochrometer, in a KCl solution of 0.15 mol/liter concentration, and the pH change at that time was examined and compared with the pH change of proteoliposomes with conventional bacteriorhodopsin alone containing no bacteriorhodopsin analogue. As the result, in the mixed proteoliposomes, an equal proton active transportability was exhibited in the incident wavelength region from 450 nm to 570 nm, thus indicating that the use range of controlled incident light can be broadened to great extent.

EXAMPLE 2

By use of a nitrocellulose filter subjected to the dipping treatment in 10 mg asolectin/ml decane solution as the dialysis membrane, an asolectin layer was formed on the filter surface. Proteoliposomes having retinal containing bacteriorhodopsin and naphthylretinal containing bacteriorhodopsin respectively as the chromophore groups were mixed, and by use of an aqueous solution containing 0.15 mol KCl/liter and 20 mmol $CaCl_2$/liter as the internal liquid and an aqueous 0.15 mol KCl/liter solution of pH 7.0 as the external liquid, dialysis treatment was carried out until the pH became constantly 7.0. By this operation, a membrane 1, in which a protein was adsorbed and fused onto the nitrocellulose filter surface as schematically shown in FIG. 3, was obtained. With this membrane as the diaphragm, a chamber separating the two components was constituted and a 0.15 mol KCl/liter solution was filled therein. Next, when the incident wavelength and the proton concentration permeating through the diaphragm were measured with a pH electrode, it was ascertained that the proton permeability of this membrane functioned for the incident light from about 440 nm to about 570 nm. Thus, a plane membrane having the range of controlled incident light broadened to great extent could be constituted.

EXAMPLE 3

Purple membrane was extracted in the same manner as in Example 1, dissolved in 25% by weight solution of dimethylformamide to form a spreading solution and spread in a Langumuir trough in conventional manner. By use of a nitrocellulose filter adhered onto a glass substrate, monomolecular film of purple membrane was adhered onto the filter surface by the vertical dipping method. The above filter was incubated in a solution of the proteoliposome having the chromophore group replaced with naphthylretinal to effect adsorption and fusion. As schematically shown in FIG. 4, the film 1 thus constituted has two different kinds of proteins co-present therein. The nitrocellulose filter adhered with the purple monomolecular layer and the protein liposome fused thereto was examined for proton permeability by photoirradiation similarly as in Example 2. As the result, it was confirmed that the directions of proton permeability became opposite to each other at the wavelengths of incident light of 450 nm and 550 nm.

EXAMPLE 4

The purple membrane extracted from *Halobacterium halobium* R1 strain by the method of Oesterhelt et al as described above was treated with a surfactant Triton X-100 (manufactured by Wako Junyaku Kogyo Co.) according to the method of Huang et al to remove lipids from the extracted purple membrane and obtain bacteriorhodopsin which was the photoreceptive protein component. Chromophore group of the bacteriorhodopsin thus purified was substituted with naphthylretinal which was a kind of retinal analogues according to the method of Tokunaga et al [F. Tokunaga and T. Iwasa, Membrane, 9, 73 (1984)]. While the maximum absorption wavelength of bacteriorhodopsin was around 560 nm, the maximum absorption wavelength of the bacteriorhodopsin analogue having naphthylretinal as the chromophore group became to be distributed from 442 nm to 503 nm depending on the mixing ratio. The bacteriarhodopsin analogue exhibited a proton active transport activity by photoirradiation similarly as bacteriorhodopsin. The bacteriorhodopsin analogue by use of naphthylretinal obtained as described above and the soyben phospholipid puified by the method of Y. Kagawa as mentioned above were reconstituted as proteoliposome based on the method of Huang et al as described above. The proteoliposome was irradiated with amonochromatic visible light obtained from a mercury lamp light passing through a monochrometer, in a KCl solution of 0.15 mol/liter concentration, and the pH change at that time was examined and compared with the pH change of proteoliposomes with conventional bacteriorhodopsin alone containing no bacteriorhodopsin analogue. As the result, in the proteoliposome having the bacteriorhodopsin analogues incorporated therein, an equal proton active transportability was exhibited in the incident wavelength region from around 440 nm to around 500 nm, thus indicating that the use range of controlled incident light can be broadened to great extent by permitting a system by use of conventional bacteriorhodopsin to be co-present.

Next, the bacteriorhodopsin purified according to the method of K. S. Huang as mentioned above, valinomycin, a kind of ionophore as mentioned above, having a selective permeability to potassium ion at 2 μM per bacteriorhodosin 0.1 mg/ml and the soybean phospholipid asolectin purified according to the method of Y. Kagawa et al at 8 to 12 mg/ml per bacteriorhodopsin 0.1 mg/ml, all of the three, were reconstituted as a planar membrane.

Further, the proteoliposome containing the bacteriorhdopsin analogue prepared by the method of K. S. Huang as mentioned above was fused and adsorbed onto the lipid plane membrane containing bacteriorhodopsin and valinomycin prepared by the method as described above so that the directionality of proton transoport became exactly opposite thereto. At this time, the directionalities of proton transport were respectively maintained.

Figure 9:
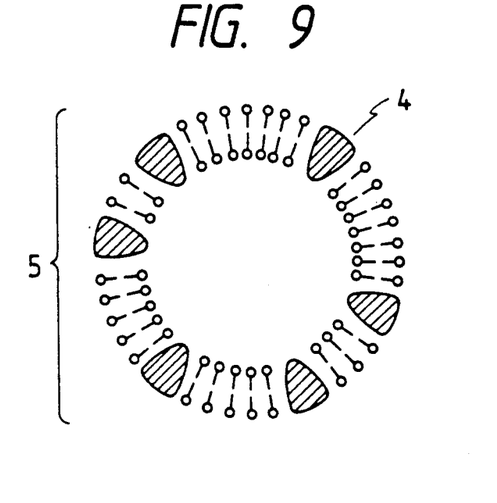
FIGS. 9 through 12 are schematic diagrams for illustration of Examples 4 to 6.
Figure 10:
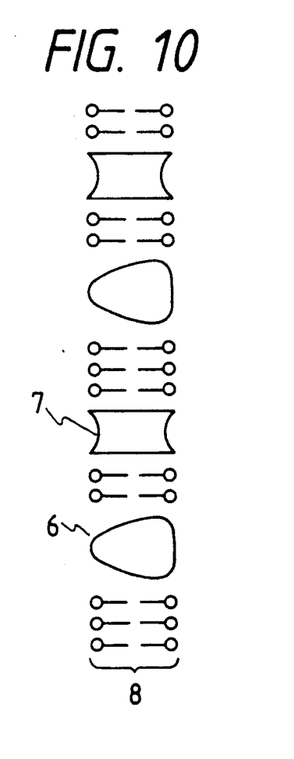
Figure 11:
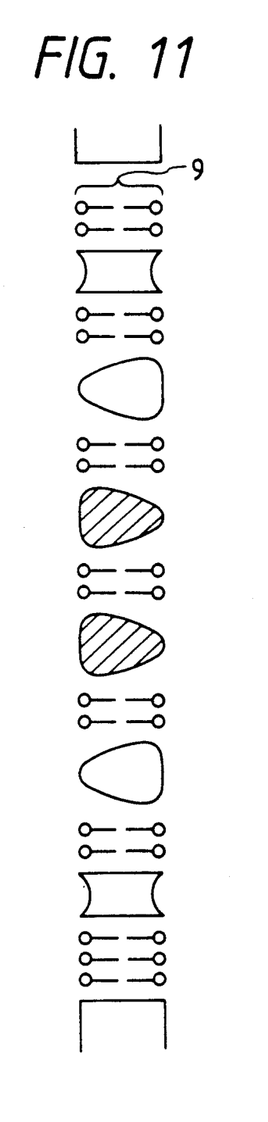
Figure 12:
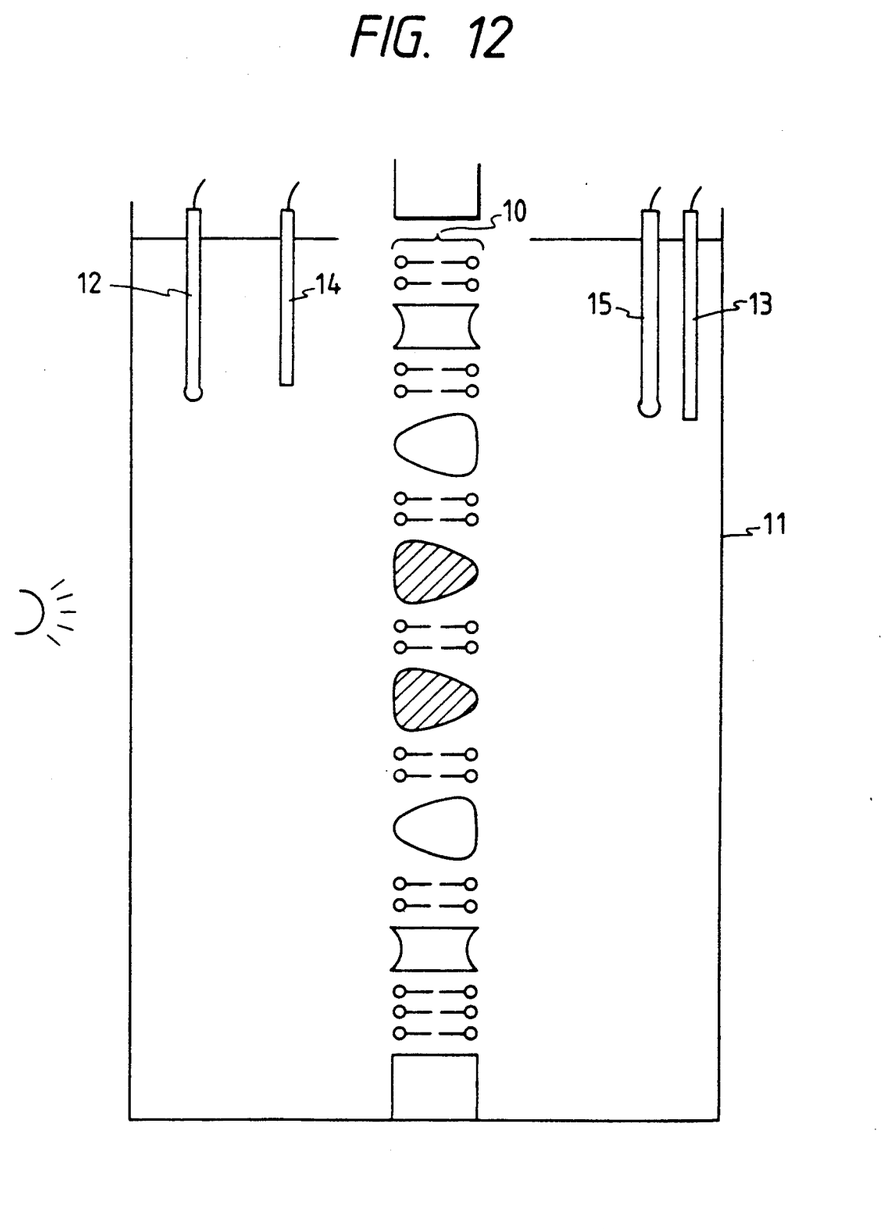

FIG. 9 through FIG. 12 are schematic illustrations representing best the specific feature of the first embodiment of the present invention. In FIG. 9, 4 is the bacteriorhodopsin analogue by use of naphthylretinal, and 5 is proteoliposome containing 4. In FIG. 10, 6 is the bacteriorhodopsin, 7 is valinomycin, a kind of ionophore, 8 is lipid bilayer plane film comprising soybean phospholipid. FIG. 11 shows a fused, adsorbed and cleaved view of 5 in FIG. 9 from the left side of 8 in FIG. 10. FIG. 12 shows the membrane as a whole in FIG. 11, which is dipped in a bath tank 11 comprising a light-transmissive material and left to stand stationarily. In FIG. 12, bacteriorhodopsin is held in the direction of transporting protons from the left to the right, and the bacteriorhodopsin analogue from the right to the left. In FIG. 12, on the left side separated with the membrane 10 dipped in the liquid, potassium ion is contained, while on the right side no potassium is contained. However, the osmotic pressures on both sides of 10 are made equal. On both sides of 10, pH electrodes 12, 13 and potassium ion elctrodes 14, 15 are dipped.

Next, when a visible light of 560 nm was irradiated from the left side of the bath tank 11, the value of the pH electrode 12 was elevated, while the value of 5 dropped down. On the other hand, the value of the ion electrode 14 dropped down, while the value of 15 was elevated.

Next, the irradiated light of 560 nm was extinguished, and after the values of the pH electrodes were returned to those before irradiation, a light of 442 nm was irradiated from the left side. As the result, the value of the pH electrode 12 dropped down, while the value of 13 was elevated. The values of the ion electrodes 14 and 15 continued to be varied.

Here, it was shown that a bidirectional proton transport was controlled by photoirradiation with different wavelengths, and further a permeability of potassium ion was varied at the same time by valinomycin with the concentration gradient by proton transport as the driving force.

EXAMPLE 5

In Example 5, variations of the bidirectional proton transport and the potassium ion permeability by photoirradiation with different wavelengths as previously shown in Example 4 were examined not only for potassium ion, but also for sodium ion.

In FIG. 10, by use of 2 μM of monendin (per bacteriorhodopsin 0.1 mg/ml) which was an ionophore of sodium ions for the ionophore 7, a planar membrane was prepared in the same manner as described in Example 4. FIG. 11 shows a fused, adsorbed and cleaved view of 5 in FIG. 9 which is proteoliposome containing the bacteriorhodopsin analogue by use of naphthylretinal from the left side of 8 in FIG. 10. FIG. 12 shows the membrane as a whole in FIG. 11, which is dipped in a bath tank 11 comprising a light-transmissive material and left to stand stationarily. In FIG. 12, bacteriorhodopsin is held in the direction of transporting protons from the left to the right, and the bacteriorhodopsin analogue from the right to the left. In FIG. 12, on the left side separated with the membrane 10 dipped in the liquid, sodium ion was contained, while on the right side no sodium was contained. However, the osmotic pressures on both sides of 10 are made equal. On both sides of 10, pH electrodes 12, 13 and sodium ion elctrodes 14, 15 are dipped.

Next, when a visible light of 560 nm was irradiated from the left side of the bath tank 11, the value of the pH electrode 12 was elevated, while the value of 13 dropped down. On the other hand, the value of the ion electrode 14 dropped down, while the value of 15 was elevated.

Next, the irradiated light of 560 nm was extinguished, and after the values of the pH electrodes were returned to those before irradiation, a light of 442 nm was irradiated from the left side. As the result, the value of the pH electrode 12 dropped down, while the value of 13 was elevated. The values of the ion electrodes 14 and 15 continued to be varied.

Here, it was shown that bidirectional proton transport was controlled by photoirradiation with different wavelengths, and further permeability of sodium ions was varied at the same time by monendin with the concentration gradient by proton transport as the driving force.

EXAMPLE 6

In Example 6, variations of the bidirectional proton transport and the potassium ion permeability by photoirradiation with different wavelengths as previously shown in Example 4 were examined not only for potassium ion, but also for magnesium ion.

In FIG. 10, by use of 2 μM of A23187 (per bacteriorhodopsin 0.1 mg/ml) which is an ionophore of magnesium ions for the ionophore 7, a planar membrane was prepared in the same manner as described in Example 4. FIG. 11 shows a fused, adsorbed and cleaved view of 5 in FIG. 9 which is proteoliposome containing the analogue bacteriorhodopsin by use of naphthylretinal from the left side of 8 in FIG. 10. FIG. 12 shows the membrane as a whole in FIG. 11, which is dipped in a bath tank 11 comprising a light-transmissive material and left to stand stationary. In FIG. 12, bacteriorhodopsin is held in the direction of transporting protons from the left to the right, and the bacteriorhodopsin analogue from the right to the left. In FIG. 12, on the left side separated with the membrane 10 dipped in the liquid, magnesium ion is contained, while on the right side no magnesium is contained. However, the osmotic pressures on both sides of 10 are made equal. On both sides of 10, pH electrodes 12, 13 and magnesium ion elctrodes 14, 15 are dipped.

Next, when a visible light of 560 nm was irradieated from the left side of the bath tank 11, the value of the pH electrode 12 was elevated, while the value of 13 dropped down. On the other hand, the value of the ion electrode 14 dropped down, while the value of 15 was elevated.

Next, the irradiated light of 560 nm was extinguished, and after the values of the pH electrodes were returned to those before irradiation, a light of 442 nm was irradiated from the left side. As the result, the value of the pH electrode 12 dropped down, while the value fo 13 was elevated. The values of the ion electrodes 14 and 15 continued to be varied.

Here, it was shown that a bidirectional proton transport was controlled by photoirradiation with different wavelengths, and further permeability of magnesium ion was varied at the same time by A23187 with the concentration gradient by proton transport as the driving force.

According to the present invention, an ion permeable membrane having selective ion permeability by photoirradiation can be constituted by utilizing groups of substances which transport ions by absorption of light, and also the wavelength region of incident visible light can be set at a broad range when the membrane ion permeability is controlled by photoirradiation, whereby it becomes also possible to expand the effective wavelength region.

Further by holding an ionophore together with the group of substances transporting ions within the same membrane, permeabilities of different kinds of ions can be controlled by photoirradiation, without limitation to one kind.

Further, it becomes also possible to switch the direction of ion permeation through the permeable membrane of the present invention depending on the incident wavelength and also vary it reversibly. By doing so, it is also possible to improve the wavelength selectivity of an ion permeability to great extent.

Since the ion concentration difference between ion permeable membranes can be converted easily to electrical signals with ion electrodes, etc., the present invention can be greatly expected to make contributions to constitution of photoelectric converting devices in the field of optical information processing industry or optoelectronics, as in the case of converting optical signals to electrical signals.

What is claimed is:

1. An ion permeable membrane, comprising two or more groups of substances having selected different sensitive wavelength regions and being capable of transporting ions upon absorption of light in a lipid membrane, whereby ion permeability of said membrane is controlled by irradiating said membrane with a light having a selected wavelength.

2. The ion permeable membrane according to claim 1, wherein said substances are photoreceptive proteins and derivatives thereof.

3. The ion permeable membrane according to claim 1, wherein said substances perform an ion active transport on light irradiation.

4. The ion permeable membrane according to claim 2, wherein said photoreceptive protein is rhodopsin, porphyropsin or iodopsin.

5. The ion permeable membrane according to claim 2, wherein said photoreceptive protein is bacteriorhodopsin or halorhodopsin.

6. The ion permeable membrane according to claim 1, wherein said substances are oriented in the lipid membrane so that the ion may become permeable in the same direction.

7. The ion permeable membrane according to claim 1, wherein said substances are oriented in the lipid membrane so that a kind of substance may transport ion in the same direction.

8. The ion permeable membrane according to claim 1, wherein said substances are oriented in the lipid membrane so that a kind of substance may transport ion in the opposite direction to another kind of substance.

9. The ion permeable membrane according to claim 1, wherein said ion permeable membrane is formed on a porous substrate.

10. The ion permeable membrane according to claim 9, wherein said porous substrate is paper or fabric made of collagen, cellulose, or porous glass.

11. An ion permeable membrane, comprising ionophore and two or more group of substances having selected different sensitive wavelength regions and being capable of transporting ions upon absorption of light in a lipid membrane, whereby ion permeability of said membrane is controlled by irradiating said membrane with a light having a selected wavelength.

12. The ion permeable membrane according to claim 11, wherein said substances are photoreceptive proteins and derivatives thereof.

13. The ion permeable membrane according to claim 11, wherein said substances perform an ion active transport on light irradiation.

14. The ion permeable membrane according to claim 12, wherein said photoreceptive protein is rhodopsin, porphyropsin or iodopsin.

15. The ion permeable membrane according to claim 12, wherein said photoreceptive protein is bacteriorhodopsin or halorhodopsin.

16. The ion permeable membrane according to claim 11, wherein said substances are oriented in the lipid membrane so that the ion may become permeable in the same direction.

17. The ion permeable membrane according to claim 11, wherein said substances are oriented in the lipid membrane so that a kind of substance may transport ion in the same direction.

18. The ion permeable membrane according to claim 11, wherein said substances are oriented in the lipid membrane so that a kind of substance may transport ion in the opposite direction to another kind of substance.

19. The ion permeable membrane according to claim 11, wherein said ion permeable membrane is formed on a porous substrate.

20. The ion permeable membrane according to claim 19, wherein said porous substrate is paper or fabric made of collagen, cellulose, or porous glass.

21. The ion permeable membrane according to claim 11, wherein said ionophore is selected from oligopeptides, polycorals, polyetherpolyamines or cyclams.

22. An ion transport method utilizing an ion permeable membrane, which comprises varying the ion permeability of said ion permeable membrane by irradiating a light on the ion permeable membrane of claim 1 by selecting the wavelength of said light.

23. An ion transport method utilizing an ion permeable membrane, which comprises varying the ion permeability of said ion permeable membrane by irradiating a light on the ion permeable membrane of claim 11 by selecting the wavelength of said light.

24. An ion transport device, comprising an ion permeable membrane, which comprises two or more groups of substances having selected different sensitive wavelength regions and being capable of transporting ions upon absorption of light in a lipid membrane and a means for sensing an ion concentration change, whereby ion permeability of said membrane is controlled by irradiating said membrane with a light having a selected wavelength.

25. An ion transport device, comprising an ion permeable membrane, which comprises an ionophore and two or more group of substances having selected different sensitive wavelength regions and being capable of transporting ions upon absorption of light in a lipid membrane and a means for sensing an ion concentration change, whereby ion permeability of said membrane is controlled by irradiating said membrane with a light having a selected wavelength.

26. An ion transport device, comprising an ion permeable membrane, which comprises two or more groups of substances having selected different sensitive wavelength regions and being capable of transporting ions upon absorption of light in a lipid membrane and a vessel containing a solution for dipping said ion permeable membrane, whereby ion permeability of said membrane is controlled by irradiating said membrane with a light having a selected wavelength.

27. An ion transport device, comprising an ion permeable membrane, which comprises an ionophore and two or more groups of substances having selected different sensitive wavelength regions and being capable of transporting ions upon absorption of light in a lipid membrane and a vessel containing a solution for dipping said ion permeable membrane, whereby ion permeability of said membrane is controlled by irradiating said membrane with a light having a selected wavelength.

* * * * *

UNITED STATES PATENT AND TRADEMARK OFFICE
CERTIFICATE OF CORRECTION

PATENT NO. : 5,041,224  
DATED : August 20, 1991  
INVENTOR(S) : Junji Ohyama, et al Page 1 of 4

It is certified that error appears in the above-identified patent and that said Letters Patent is hereby corrected as shown below:

TITLE PAGE:
IN [30] FOREIGN APPLICATION PRIORITY DATA

Insert:   --Mar. 18, 1989  [JP]  Japan ....... 1-067365--.

IN [56] REFERENCES CITED

OTHER PUBLICATIONS, Under Patent Abstracts, "Appln. No. 1-180854" should read --Appln. No. 1-80854--.

COLUMN 1

Line 23, "so called" should read --so-called--.
   Line 24, "potential" should read --potential,--.
   Line 30, "as sensor" should read --as a sensor--.
   Line 31, "in biological" should read --in a biological--.
   Line 37, "A" should read --An--.
   Line 39, "maintaining and" should read --and maintaining--.
   Line 46, "not limited" should read --not be limited--.
   Line 50, "an" should be deleted.
   Line 65, "wave length" should read --wavelength--.

COLUMN 2

Line 43, "protein" should read --proteins--.
   Line 53, "that" should be deleted.
   Line 67, "so called" should read --so-called--.

COLUMN 3

Line 9, "preferably" should be deleted.
   Line 26, "(1980)," should read --1980)),-- and "bacteriorhodopsin.)" should read --bacteriorhodopsin.--.

UNITED STATES PATENT AND TRADEMARK OFFICE
CERTIFICATE OF CORRECTION

PATENT NO. : 5,041,224
DATED : August 20, 1991
INVENTOR(S) : Junji Ohyama, et al It is certified that error appears in the above-identified patent and that said Letters Patent is hereby corrected as shown below:

COLUMN 3

Line 47, "in rhodopsin" should read --of bacteriorhodopsin--.

COLUMN 4

Line 6, "these knowledges" should read --this information--.
    Line 11, "substance" should be deleted.
    Line 16, "photorecptive" should read --photoreceptive--.

COLUMN 5

Line 17, "double layers" should read --bilayer--.
    Line 46, "method" should read --method or--.

COLUMN 7

Line 18, "photoreceptive 1a and 1b" should read --photoreceptive proteins 1a and 1b--.
    Line 65, "component," should read --component--.
    Line 68, "analogues" should read --analogue--.

COLUMN 8

Line 45, "components" should read --compartments--.
    Line 59, "Langumuir" should read --Langmuir--.

COLUMN 9

Line 18, "analogues" should read --analogue--.

UNITED STATES PATENT AND TRADEMARK OFFICE
CERTIFICATE OF CORRECTION

PATENT NO. : 5,041,224
DATED : August 20, 1991
INVENTOR(S) : Junji Ohyama, et al Page 3 of 4

It is certified that error appears in the above-identified patent and that said Letters Patent is hereby corrected as shown below:

COLUMN 9

Line 26, "teriarhodopsin" should read --teriorhodopsin--.
    Line 30, "soyben" should read --soybean--.
    Line 34, "amonochromatic" should read --a monochromatic--.
    Line 52, "bacteriorhodosin" should read --bacteriorhodopsin--.
    Line 58, "orhdopsin" should read --orhodopsin--.
    Line 63, "transoport" should read --transport--.

COLUMN 10

Line 18, "elctrodes" should read --electrodes--.
    Line 21, "5" should read --15--.

COLUMN 11

Line 41, "elctrodes" should read --electrodes--.
    Line 43, "irradieated" should read --irradiated--.
    Line 53, "fo" should read --of--.

COLUMN 12

Line 3, "Further" should read --Further,--.
    Line 62, "group" should read --groups--.

UNITED STATES PATENT AND TRADEMARK OFFICE
CERTIFICATE OF CORRECTION

PATENT NO. : 5,041,224

DATED : August 20, 1991

INVENTOR(S) : Junji Ohyama, et al

It is certified that error appears in the above-identified patent and that said Letters Patent is hereby corrected as shown below:

<u>COLUMN 14</u>

Line 15, "group" should read --groups--.

Signed and Sealed this

Thirteenth Day of April, 1993

Attest:

STEPHEN G. KUNIN

*Attesting Officer*          Acting Commissioner of Patents and Trademarks